(12) United States Patent
Rusznak

(10) Patent No.: US 9,936,798 B2
(45) Date of Patent: Apr. 10, 2018

(54) TOOTH BRUSH AND FLOSSING AID COMBINATION

(71) Applicant: Zoltan Rusznak, Ashburn, VA (US)

(72) Inventor: Zoltan Rusznak, Ashburn, VA (US)

(*) Notice: Subject to any disclaimer, the term of this patent is extended or adjusted under 35 U.S.C. 154(b) by 182 days.

(21) Appl. No.: 14/842,331

(22) Filed: Sep. 1, 2015

(65) Prior Publication Data

US 2015/0366335 A1 Dec. 24, 2015

Related U.S. Application Data

(63) Continuation-in-part of application No. 13/910,951, filed on Jun. 5, 2013.

(51) Int. Cl.
| | |
|---|---|
| *A45D 44/18* | (2006.01) |
| *A46B 15/00* | (2006.01) |
| *A61C 15/04* | (2006.01) |

(52) U.S. Cl.
CPC ........ *A46B 15/0071* (2013.01); *A61C 15/046* (2013.01)

(58) Field of Classification Search
CPC .......................... A46B 15/00; A46B 15/0071
USPC ........................ 132/309, 308, 323
See application file for complete search history.

(56) References Cited

U.S. PATENT DOCUMENTS

| | | | |
|---|---|---|---|
| 1,627,525 A | 5/1927 | Munro | |
| 1,695,238 A | 12/1928 | Kalenoff | |
| 2,113,439 A | 4/1938 | Bean | |
| 2,354,454 A | 7/1944 | Geffner | |
| 2,468,298 A | 4/1949 | Kahn | |
| 2,664,093 A * | 12/1953 | Carpenter | A61C 15/046 |
| | | | 132/323 |
| 3,850,182 A | 11/1974 | Clark, Jr. | |
| 3,939,853 A | 2/1976 | Spanondis | |
| 4,016,891 A | 4/1977 | Kupperman | |

FOREIGN PATENT DOCUMENTS

WO  2009072277  6/2009

OTHER PUBLICATIONS

International Search Report and Written Opinion for Appl. No. PCT/US2016/045071, dated Oct. 20, 2016, 8 pages.

\* cited by examiner

*Primary Examiner* — Rachel Steitz
(74) *Attorney, Agent, or Firm* — Patent Law of Virginia, PLLC; Brian J. Teague

(57) ABSTRACT

An oral hygiene device adapted for use in the oral cavity comprises a toothbrush at one end and a flossing device at the opposite end. The flossing device comprises first and second arms and first and second floss-anchoring buttons. Each arm has a floss-receiving slot defined in a distal end. The first floss-anchoring button projects from the first arm and the second floss-anchoring button projects from the second arm. Each floss-anchoring button has two or more floss-receiving channels defined in a peripheral wall thereof.

5 Claims, 6 Drawing Sheets

TOOTH BRUSH AND FLOSSING AID COMBINATION

CROSS-REFERENCE TO RELATED APPLICATIONS

This application is a continuation-in-part of and claims priority to U.S. application Ser. No. 13/910,951, filed Jun. 5, 2013, the contents of which are incorporated herein by reference in its entirety.

FIELD OF THE INVENTION

The present disclosure relates generally to dental devices.

BACKGROUND OF THE DISCLOSURE

My background in dental field extends over a period of 15 years, working as a dentist and being faced daily by wide variety of dental needs. Brushing and flossing, and the patients non-compliance performing this routine and useful procedure for the health of the oral cavity, intrigued me for years and made me design a simple and useful combination of the two basic oral heath procedures, brushing and flossing.

Why a combination, someone will ask. It is in the human nature to perform more often both procedures, if it's presented in one simple and effortless solution.

BRIEF SUMMARY OF THE DISCLOSURE

In one embodiment of the invention, an oral hygiene device adapted for use in the oral cavity comprises a toothbrush at one end and a flossing device at the opposite end. The flossing device comprises first and second arms and first and second floss-anchoring buttons. Each arm has a floss-receiving slot defined in a distal end. The first floss-anchoring button projects from the first arm and the second floss-anchoring button projects from the second arm. Each floss-anchoring button has two or more floss-receiving channels defined in a peripheral wall thereof.

Each of the two or more floss-receiving channels may be continuous about a circumference of its respective floss-anchoring button.

Two or more floss-receiving channels may be defined in a first side of the first floss-anchoring button. Two or more floss-receiving channels may be defined in a second side of the first floss-anchoring button opposite the first side. The two or more floss-receiving channels defined in the first side of the first floss-anchoring button may not be continuous with the two or more floss-receiving channels defined in the second side of the first floss-anchoring button. Two or more floss-receiving channels may be defined in a first side of the second floss-anchoring button. Two or more floss-receiving channels may be defined in a second side of the second floss-anchoring button opposite the first side. The two or more floss-receiving channels defined in the first side of the second floss-anchoring button may not be continuous with the two or more floss-receiving channels defined in the second side of the second floss-anchoring button.

Each of the two or more floss-receiving channels may be substantially perpendicular to a longitudinal axis of its respective floss-anchoring button. Each of the two or more floss-receiving channels may be angled relative to a longitudinal axis of its respective floss-anchoring button.

Each arm may be curved in at least two planes. Each arm may be tapered. Each arm may be round in cross-section.

In an alternative embodiment of the invention, an oral hygiene device adapted for use in the oral cavity comprises a toothbrush at one end and a flossing device at the opposite end. The flossing device comprises first and second arms. Each arm has a floss-receiving slot defined in a distal end. Each arm has two or more floss-receiving channels defined therein.

The oral hygiene device may further comprise first and second floss-positioning buttons. The first floss-positioning button projects from the first arm at a position that is distal to the two or more floss-receiving channels. The second floss-positioning button projects from the second arm at a position that is distal to the two or more floss-receiving channels. Each floss-positioning button has a head portion and a neck portion, a diameter of the neck portion being smaller than a diameter of the head portion.

Each of the two or more floss-receiving channels may be continuous about a circumference of its respective arm.

Two or more floss-receiving channels may be defined in a first side of the first arm. Two or more floss-receiving channels may be defined in a second side of the first arm opposite the first side. The two or more floss-receiving channels defined in the first side of the first arm may not be continuous with the two or more floss-receiving channels defined in the second side of the first arm. Two or more floss-receiving channels may be defined in a first side of the second arm. Two or more floss-receiving channels may be defined in a second side of the second arm opposite the first side. The two or more floss-receiving channels defined in the first side of the second arm may not be continuous with the two or more floss-receiving channels defined in the second side of the second arm.

Each of the two or more floss-receiving channels may be substantially perpendicular to a longitudinal axis of its respective arm. Each of the two or more floss-receiving channels may be angled relative to a longitudinal axis of its respective arm.

Each arm may be curved in at least two planes. Each arm may be tapered. Each arm may be round in cross-section.

BRIEF DESCRIPTION OF THE SEVERAL VIEWS OF THE DRAWINGS

The foregoing summary, as well as the following detailed description of the disclosure, will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities shown. In the drawings.

DETAILED DESCRIPTION OF THE DISCLOSURE

Figure 1:
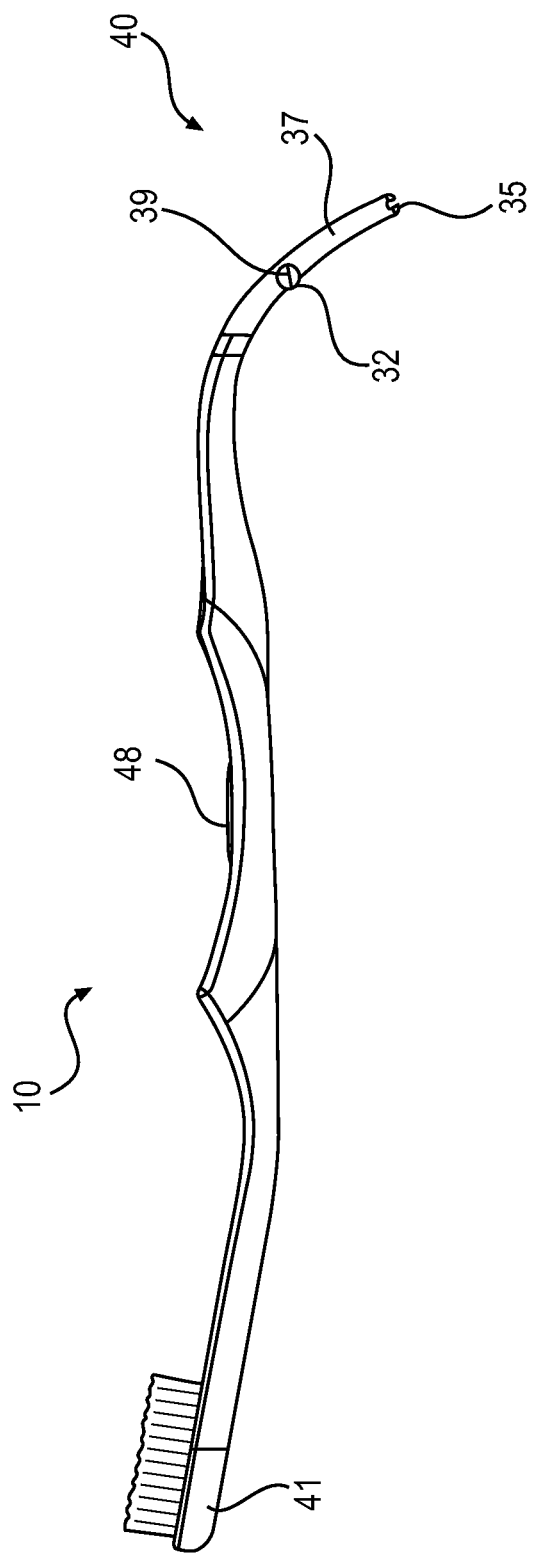
FIG. 1 is a side view of a combination toothbrush and flossing device, in accordance with embodiments of the invention.
Figure 2:
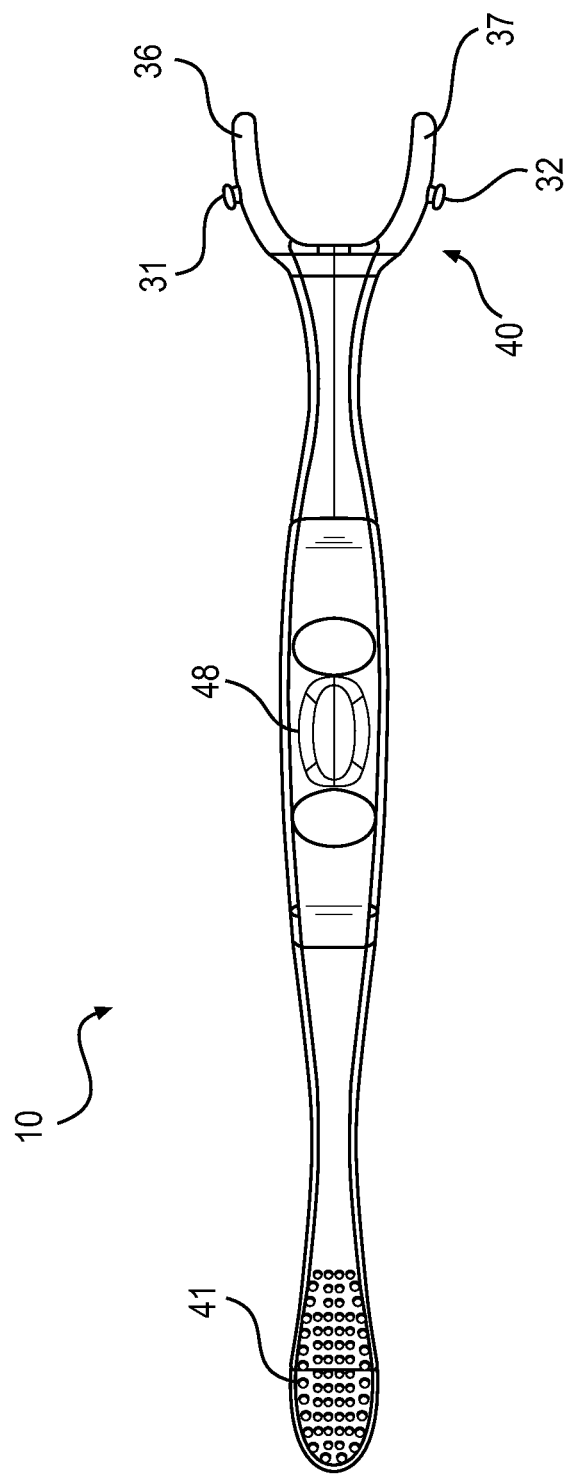
FIG. 2 is a top view of the device of FIG. 1.
Figure 3:
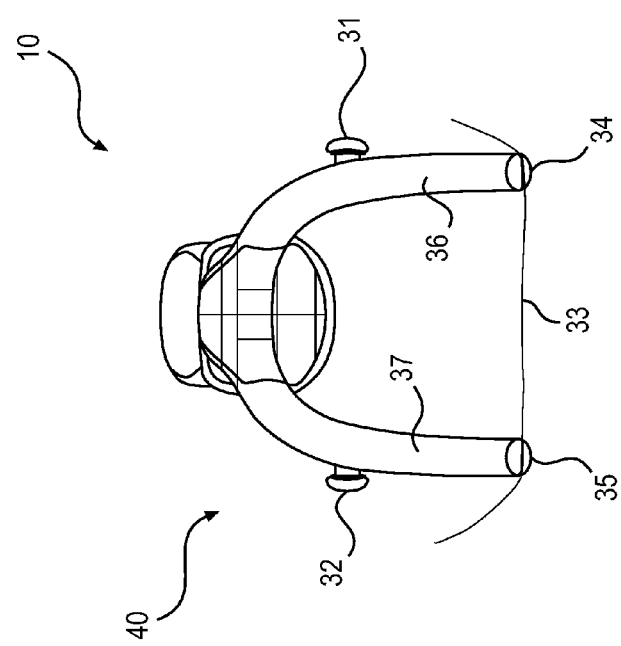
FIG. 3 is a flossing end view of the device of FIG. 1.
Figure 4:
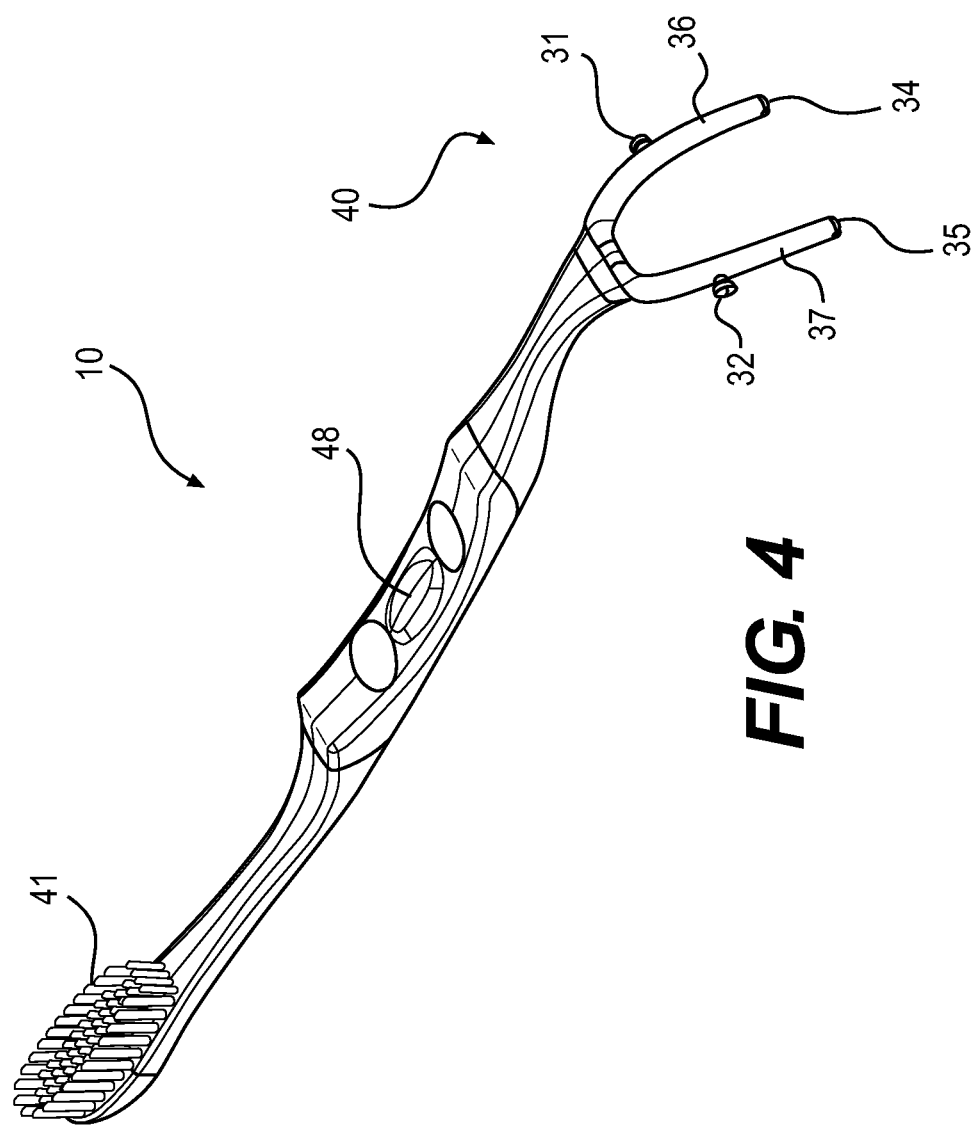
FIG. 4 is a perspective view of the device of FIG. 1.

Certain terminology is used in the following description for convenience only and is not limiting. The words "lower," "bottom," "upper," and "top" designate directions in the drawings to which reference is made. The words "inwardly," "outwardly," "upwardly" and "downwardly" refer to directions toward and away from, respectively, the geometric center of the device, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

The present solution represents a sophisticated ergonomic design of a dental device 10 having a toothbrush 41 on one end, and the flossing aid 40 on the opposite end. 31

Flossing is a daily routine, aimed to preserve the periodontal health (gum disease), and prevent the formation of tooth decay and bad breath.

There are certain dental hygiene devices that incorporate a fixed portion of the dental floss, designed for single use. Some of them have the ability of replacing the head that contains the floss.

The present solution incorporates the use of the toothbrush head 41 on one end of the device, and a flossing aid 40 on the opposite end, that allows the replacement of the floss 33 after each hygiene procedure.

The ergonomic design of the present device, the slight curvature of the neck of the brush head, and the curvature of the opposite end that holds the floss, has been tested and conforms with the average arch of the maxillary (upper) teeth, and the mandibular (lower) teeth.

Furthermore, the curvature of the flossing end has been designed and tested, to allow the operator to reach the most difficult area in the oral cavity, without any exceptional dexterity, and effort, making flossing a very desirable procedure.

Furthermore, the fork area 40 of the device, and the opening between the arms 36, 37 has optimum size, taking in consideration the average size and position of the teeth in the oral cavity, providing this way a comfortable fit and feel during the hygiene procedure (flossing).

It is a known fact that the floss is not reusable, and should be discarded after each use, therefore the present device provides a fast and simple way of replacing it.

The operator chooses the length of floss and, with a simple motion, can insert it in a retention slot 39 present on the button 32 from the left arm 37, then will rotate the floss around the button and inserts it the opposite direction into the same slot, then takes the floss over the slot 35 present on the tip of the left arm 32, takes it across the opening of the fork into the slot 34 present on the tip of the opposite arm 36 of the fork, then into the retention slot on the button 31 on the side of the arm 36, will rotate the floss and lock it into the position.

This way the floss 33 will stay under tension and will not slide nor lose tension during the flossing procedure.

The present device, will accept any type of floss currently on the market, round, flat, waxed or unwaxed. A silicon type handle insert 48 provides better grip, feel, and ergonomics.

The present device provides an ergonomically, simple to use and economical solution.

Figure 5:
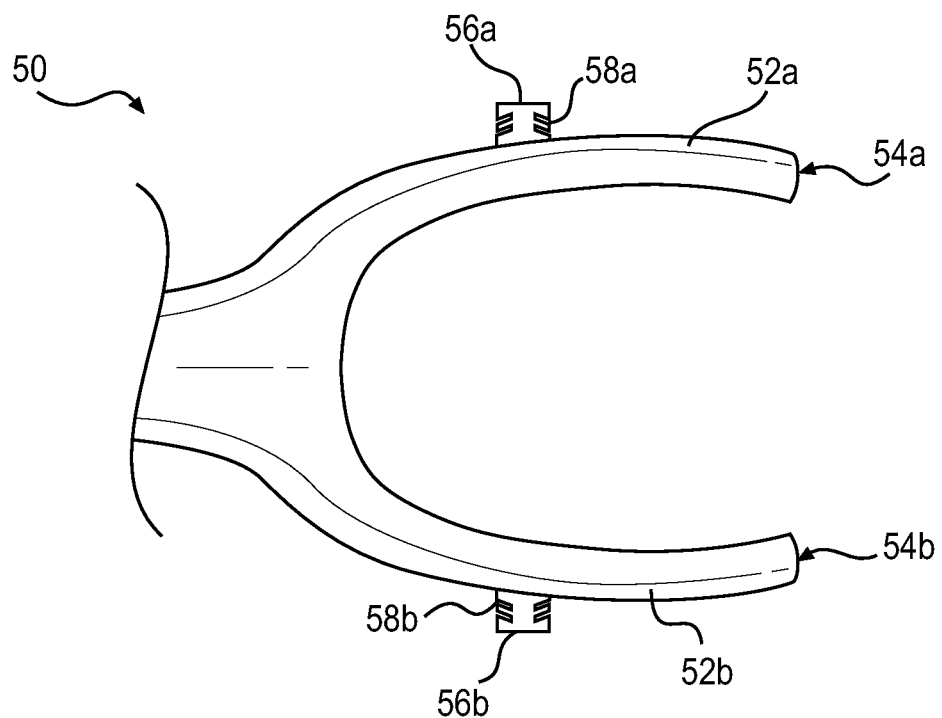
FIG. 5 is a top view of a flossing end of a combination toothbrush and flossing device, in accordance with alternative embodiments of the invention.
Figure 6:
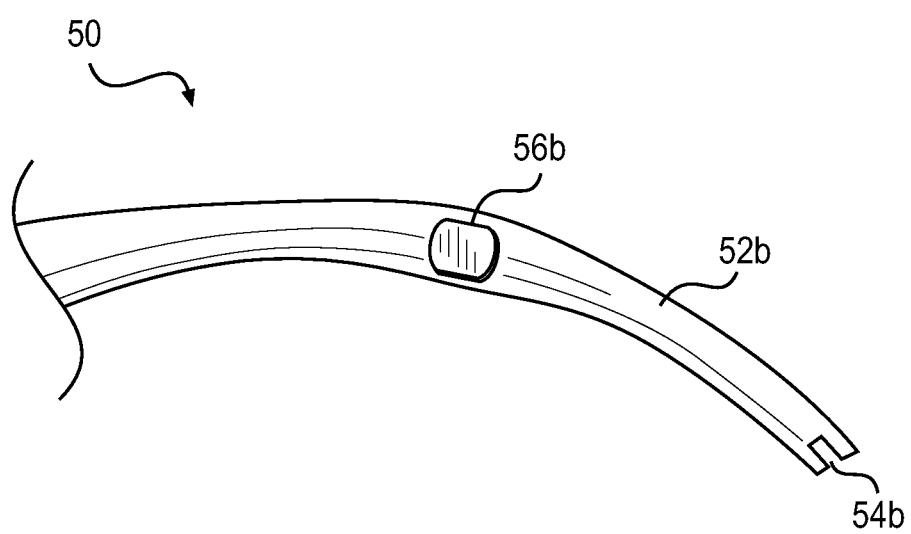
FIG. 6 is a side view of the device of FIG. 5.

Referring now to FIGS. 5 and 6, an alternative embodiment of a combination toothbrush and flossing device 50 is illustrated. Device 50 is very similar to device 10, however the floss retention buttons have a different structure. Only the flossing end of device 50 is illustrated, as the handle and toothbrush end may be identical to that of device 10. The flossing end of device 50 comprises two arms 52a, 52b. Each arm has a floss guide slot 54a, 54b defined in the tip of each arm. Each arm also has a floss retention button 56a, 56b projecting laterally from the side of each arm. Each floss retention button 56a, 56b has two or more floss-receiving channels 58a, 58b defined in the distal and proximal sides of each button ("distal" and "proximal" as used to describe the sides of the buttons refers to the sides of the buttons facing, respectively, the distal and proximal ends of the arms 54a, 54b). The top and bottom sides of each button may be flat (as seen in FIG. 6) and may not include the channels (i.e., the channels may not extend around the entire circumference of the buttons). Alternatively, the floss-receiving channels may be defined around the entire circumference of the buttons (not illustrated). Relative to the longitudinal axis of each button, the channels 58a, 58b may be substantially perpendicular, may be angled upward, or may be angled downward (such downward angling of the channels is illustrated in FIG. 5).

To secure a length of floss to device 50, a user wraps a first end of the floss two or more times around button 56a, such that the floss engages at least one channel 58a (and preferably at least two channels) on each side of button 56a. The user then extends the floss around the distal end of arm 52a, ensuring that the floss engages slot 54a, across the opening between the two distal ends of the arms, and around the distal end of arm 52b, ensuring that the floss engages slot 54b. The user then wraps a second end of the floss two or more times around button 56b, such that the floss engages at least one channel 58b (and preferably at least two channels) on each side of button 56b. Having two or more floss-receiving channels 58a, 58b makes it easier and quicker for a user to secure the two ends of the floss to the buttons 56a 56b, and makes for more secure retention of the floss. Additionally, having two or more floss-receiving channels 58a, 58b enables the floss to be secured to the buttons without having an end slot 39 as in the embodiment of FIGS. 1-4.

Figure 7:
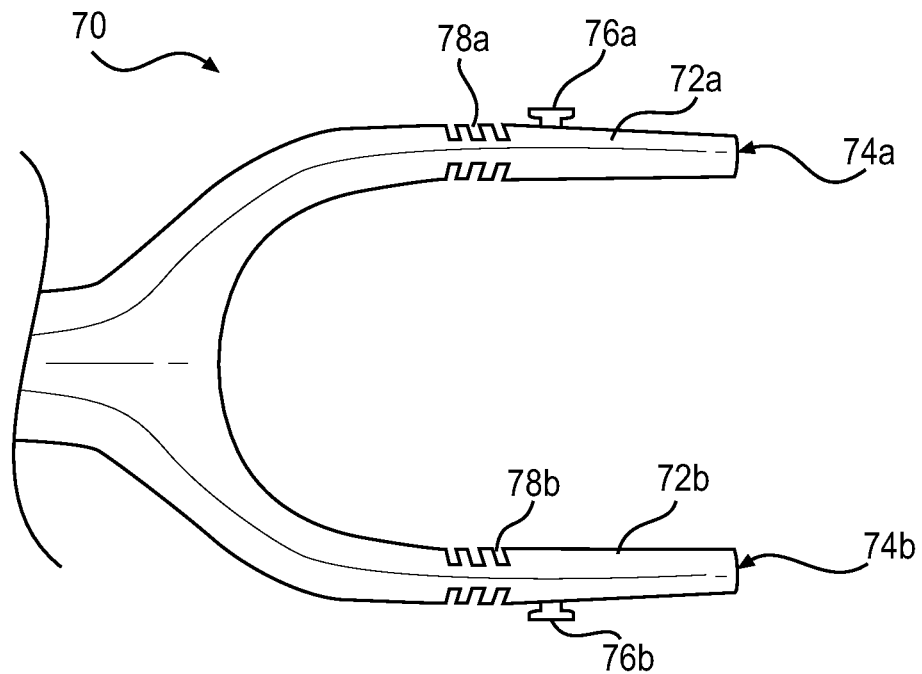
FIG. 7 is a top view of a flossing end of a combination toothbrush and flossing device, in accordance with alternative embodiments of the invention.
Figure 8:
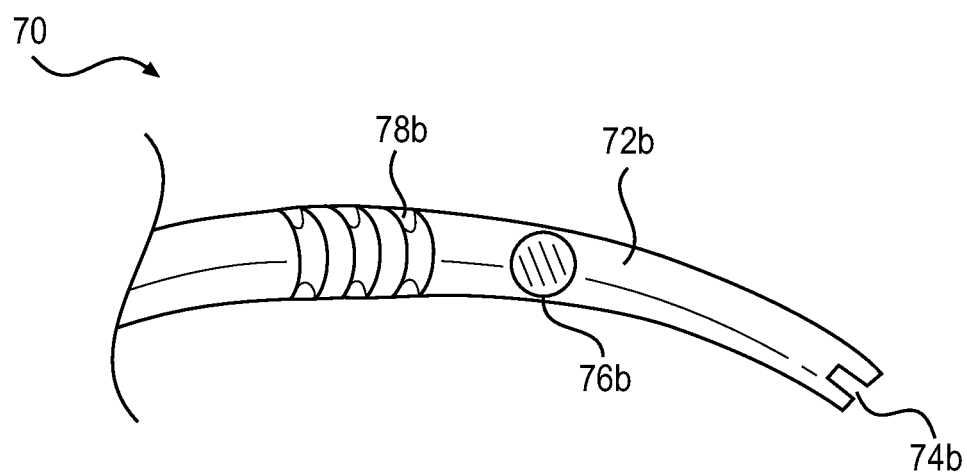
FIG. 8 is a side view of the device of FIG. 7.

Referring now to FIGS. 7 and 8, an alternative embodiment of a combination toothbrush and flossing device 70 is illustrated. Device 70 is very similar to device 10, however the floss retention buttons have a different structure and there is an additional floss-retention mechanism. Only the flossing end of device 70 is illustrated, as the handle and toothbrush end may be identical to that of device 10. The flossing end of device 70 comprises two arms 72a, 72b. Each arm has a floss guide slot 74a, 74b defined in the tip of each arm. Each arm also has a floss positioning button 76a, 76b projecting laterally from the side of each arm. Each floss positioning button 76a, 76b comprises a generally round head on top of a generally round neck, with the neck having a smaller diameter than the head such that a circumferential channel is defined between the underside of the head and the arm of the flossing device. Additionally, two or more (three are illustrated) floss retention channels 78a, 78b are defined in each arm proximal to the floss positioning buttons 76a, 76b. The channels 78a, 78b may or may not extend around the entire circumference of each arm. In the embodiment illustrated in FIGS. 7 and 8, the channels are only defined in the lateral sides of each arm (such that there are three channels on each side of each arm), while the top and bottom of each arm does not include the channels but rather is flush with the rest of the top and bottom surfaces, respectively, of the arms. Relative to the longitudinal axis of each arm, the channels 78a, 78b may be substantially perpendicular, may be angled toward the distal end of each arm, or may be angled toward the proximal end of each arm (such proximal angling of the channels is illustrated in FIGS. 7 and 8).

To secure a length of floss to device 70, a user wraps a first end of the floss two or more times around arm 72a at the location of channels 78a, such that the floss engages at least one channel 78a (and preferably at least two channels) on each side of arm 72a. The user then wraps the floss one or more times around button 76a, which helps properly position the floss. The user then extends the floss around the distal end of arm 72a, ensuring that the floss engages slot 74a, across the opening between the two distal ends of the arms, and around the distal end of arm 72b, ensuring that the floss engages slot 74b. The user then wraps the floss one or more times around button 76b, which helps properly position the floss. The user then wraps a second end of the floss two or more times around arm 72b at the location of channels 78b, such that the floss engages at least one channel 78b (and preferably at least two channels) on each side of arm 72b. Having two or more floss-receiving channels 78a, 78b defined in the arms makes it easier and quicker for a user to secure the floss, while the floss-positioning buttons helps the user quickly position the floss properly in the device.

The top surface of the head of each floss-positioning button may be flat, may be slanted (with the lower side toward the distal end of the arm and the higher side toward the proximal end of the arm, or vice versa), or may have a rounded center peak (i.e., similar to a mushroom).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

That which is claimed:

1. An oral hygiene device adapted for use in the oral cavity, the oral hygiene device comprising:
    a toothbrush at one end; and
    a flossing device at the opposite end, the flossing device comprising:
        first and second arms, each arm having a floss-receiving slot defined in a distal end; and
        first and second floss-anchoring buttons, the first floss-anchoring button projecting from the first arm and the second floss-anchoring button projecting from the second arm, each floss-anchoring button having two or more floss-receiving channels defined in a peripheral wall thereof;
    wherein two or more floss-receiving channels are defined in a first side of the first floss-anchoring button;
    wherein two or more floss-receiving channels are defined in a second side of the first floss-anchoring button opposite the first side;
    wherein the two or more floss-receiving channels defined in the first side of the first floss-anchoring button are not continuous with the two or more floss-receiving channels defined in the second side of the first floss-anchoring button;
    wherein two or more floss-receiving channels are defined in a first side of the second floss-anchoring button;
    wherein two or more floss-receiving channels are defined in a second side of the second floss-anchoring button opposite the first side; and
    wherein the two or more floss-receiving channels defined in the first side of the second floss-anchoring button are not continuous with the two or more floss-receiving channels defined in the second side of the second floss-anchoring button.

2. The oral hygiene device of claim 1, wherein each of the two or more floss-receiving channels is angled relative to a longitudinal axis of its respective floss-anchoring button.

3. The oral hygiene device of claim 1, wherein each arm is curved in at least two planes.

4. The oral hygiene device of claim 1, wherein each arm is tapered.

5. The oral hygiene device of claim 1, wherein each arm is round in cross-section.

* * * * *